US012644140B2

(12) United States Patent
Charles et al.

(10) Patent No.: US 12,644,140 B2
(45) Date of Patent: Jun. 2, 2026

(54) ENGINEERED MICROORGANISMS FOR SYNTHESIS OF POLYHYDROXYALKANOATES

(71) Applicants: Trevor Charles, Waterloo (CA); Jiujun Cheng, Waterloo (CA); Aranksha Thakor, Waterloo (CA); Nicole Schulz, Waterloo (CA)

(72) Inventors: Trevor Charles, Waterloo (CA); Jiujun Cheng, Waterloo (CA); Aranksha Thakor, Waterloo (CA); Nicole Schulz, Waterloo (CA)

( * ) Notice: Subject to any disclaimer, the term of this patent is extended or adjusted under 35 U.S.C. 154(b) by 345 days.

(21) Appl. No.: 18/322,356

(22) Filed: May 23, 2023

(65) Prior Publication Data

US 2024/0392331 A1     Nov. 28, 2024

(51) Int. Cl.
| | |
|---|---|
| *C12P 7/625* | (2022.01) |
| *C12N 9/04* | (2006.01) |
| *C12N 9/12* | (2006.01) |
| *C12N 9/24* | (2006.01) |
| *C12N 9/88* | (2006.01) |
| *C12N 15/52* | (2006.01) |

(52) U.S. Cl.
CPC ............ *C12P 7/625* (2013.01); *C12N 9/0006* (2013.01); *C12N 9/1205* (2013.01); *C12N 9/2402* (2013.01); *C12N 9/88* (2013.01); *C12N 15/52* (2013.01); *C12Y 101/01048* (2013.01); *C12Y 207/01058* (2013.01); *C12Y 302/01023* (2013.01); *C12Y 401/02021* (2013.01); *C12Y 402/01006* (2013.01)

(58) Field of Classification Search
CPC ..... C12P 7/625; C12N 9/0006; C12N 9/1205; C12N 9/2402; C12N 9/88; C12N 15/52; C12Y 101/01048; C12Y 207/01058; C12Y 302/01023; C12Y 401/02021; C12Y 402/01006
See application file for complete search history.

(56) References Cited

U.S. PATENT DOCUMENTS

2018/0057848 A1     3/2018   Ramseier et al.

FOREIGN PATENT DOCUMENTS

| | | |
|---|---|---|
| EP | 0 920 517 B1 | 11/2010 |
| EP | 2886643 A1 | 6/2015 |

OTHER PUBLICATIONS

Broun et al., Catalytic plasticity of fatty acid modification enzymes underlying chemical diversity of plant lipids. Science, 1998, vol. 282: 1315-1317. (Year: 1998).*

Catalan et al., Production of polyhydroxyalkanoates by Herbaspirillum seropedicae grown with different sole carbon sources and on lactose when engineered to express the lacZlacY genes. Enzyme Microbial Technol., 2007, vol. 40: 1352-1357. (Year: 2007).*

Devos et al., Practical limits of function prediction. Proteins: Structure, Function, and Genetics. 2000, vol. 41: 98-107. (Year: 2000).*

Salvachua et al., Metabolic engineering of Pseudomonas putida for increased polyhydroxyalkanoate production from lignin. Microbial Biotechnol., 2019, vol. 13: 290-298. (Year: 2019).*

Seffernick et al., Melamine deaminase and Atrazine chlorohydrolase: 98 percent identical but functionally different. J. Bacteriol., 2001, vol. 183 (8): 2405-2410. (Year: 2001).*

Thakor et al., Chapter 8 Isolation of Genes Encoding Carbon Metabolism Pathways from Complex Microbial Communities. Metagenomics: Methods and Protocols, Methods in Mol. Biol., Oct. 22, 2022, vol. 2555, pp. 115-123. (Year: 2022).*

Whisstock et al., Prediction of protein function from protein sequence. Q. Rev. Biophysics., 2003, vol. 36 (3): 307-340. (Year: 2003).*

Witkowski et al., Conversion of b-ketoacyl synthase to a Malonyl Decarboxylase by replacement of the active cysteine with glutamine. Biochemistry, 1999, vol. 38: 11643-11650. (Year: 1999).*

Zhou et al., Extending galactose-oxidation pathway of Pseudomonas putida for utilization of galactose-rich red macroalgae as sustainable feedstock. J. Biotechnol., 2022, vol. 348: 1-9. (Year: 2022).*

Schipper et al., Metagenome-Derived Clones Encoding Two Novel Lactonase Family Proteins Involved in Biofilm Inhibition in Pseudomonas aeruginosa. Appl. Env. Microbiol., 2009, vol. 75(1): 224-233 (Year: 2009).*

Cheng, Jiujun, et al. "Novel Polyhydroxyalkanoate Copolymers Produced in Pseudomonas Putida by Metagenomic Polyhydroxyalkanoate Synthases." Applied Microbiology and Biotechnology, vol. 100, No. 17, 2016, pp. 7611-7627, https://doi.org/10.1007/s00253-016-7666-6.

Cheng, Jiujun, et al. "A Sinorhizobium Meliloti MinE Mutant Has an Altered Morphology and Exhibits Defects in Legume Symbiosis." Microbiology, vol. 153, No. 2, 2007, pp. 375-387, https://doi.org/10.1099/mic.0.2006/001362-0.

Deininger, Prescott. "Molecular Cloning: A Laboratory Manual." Analytical Biochemistry, vol. 186, No. 1, 1990, pp. 182-183, https://doi.org/10.1016/0003-2697(90)90595-z.

Elmore, Joshua R., et al. "Engineered Pseudomonas Putida Simultaneously Catabolizes Five Major Components of Corn Stover Lignocellulose: Glucose, Xylose, Arabinose, p-Coumaric Acid, and Acetic Acid." Metabolic Engineering, vol. 62, 2020, pp. 62-71, https://doi.org/10.1016/j.ymben.2020.08.001.

Finan, T M, et al. "Second Symbiotic Megaplasmid in Rhizobium Meliloti Carrying Exopolysaccharide and Thiamine Synthesis Genes." Journal of Bacteriology, vol. 167, No. 1, 1986, pp. 66-72, https://doi.org/10.1128/jb.167.1.66-72.1986.

(Continued)

*Primary Examiner* — Ganapathirama Raghu

(74) *Attorney, Agent, or Firm* — Santosh K. Chari; CPST Intellectual Property Inc.

(57) ABSTRACT

A genetically engineered strain of *Pseudomonas* is provided, which is capable of metabolizing lactose as a sole carbon source in the production of polyhydroxyalkanoates (PHAs). A method of engineering microorganisms and a method of PHA production are also provided, wherein lactose is used as a sole carbon source.

16 Claims, 9 Drawing Sheets

Specification includes a Sequence Listing.

(56) References Cited

OTHER PUBLICATIONS

Hansen, Lars H, et al. "Chromosomal Insertion of the Entire *Escherichia coli* Lactose Operon, into Two Strains of Pseudomonas, Using a Modified Mini-Tn5 Delivery System." Gene, vol. 186, No. 2, 1997, pp. 167-173, https://doi.org/10.1016/s0378-1119(96)00688-9.

Kageyama, Yuki, et al. "Artificial Polyhydroxyalkanoate Poly[2-Hydroxybutyrate-Block-3-Hydroxybutyrate] Elastomer-like Material." Scientific Reports, vol. 11, No. 1, 2021, https://doi.org/10.1038/s41598-021-01828-9.

Li, Zibiao, et al. "Polyhydroxyalkanoates: Opening Doors for a Sustainable Future." NPG Asia Materials, vol. 8, No. 4, 2016, https://doi.org/10.1038/am.2016.48.

Loeschcke, Anita, et al. "Pseudomonas Putida—a Versatile Host for the Production of Natural Products." Applied Microbiology and Biotechnology, vol. 99, No. 15, 2015, pp. 6197-6214, https://doi.org/10.1007/s00253-015-6745-4.

Peabody, George L., et al. "Engineered Pseudomonas Putida KT2440 Co-Utilizes Galactose and Glucose." Biotechnology for Biofuels, vol. 12 295, No. 1, 2019, https://doi.org/10.1186/s13068-019-1627-0.

Schäfer, Andreas, et al. "Small Mobilizable Multi-Purpose Cloning Vectors Derived from the *Escherichia coli* Plasmids PK18 and PK19: Selection of Defined Deletions in the Chromosome of Corynebacterium Glutamicum." Gene, vol. 145, No. 1, 1994, pp. 69-73, https://doi.org/10.1016/0378-1119(94)90324-7.

Sharma, Parveen K., et al. "Kinetics of Medium-Chain-Length Polyhydroxyalkanoate Production by a Novel Isolate of Pseudomonas Putida LS46." Canadian Journal of Microbiology, vol. 58, No. 8, 2012, pp. 982-989, https://doi.org/10.1139/w2012-074.

Tsang, Yiu Fai, et al. "Production of Bioplastic through Food Waste Valorization." Environment International, vol. 127, 2019, pp. 625-644, https://doi.org/10.1016/j.envint.2019.03.076.

Volke, Daniel C., et al. "Pseudomonas Putida." Trends in Microbiology, vol. 28, No. 6, 2020, pp. 512-513, https://doi.org/10.1016/j.tim.2020.02.015.

* cited by examiner

3HB     3HV     3HHx     3HO     3HD     3HDD

Short chain length (SCL)       Medium chain length (MCL)

pTH1227 (empty vector)

pJC276 (galD, dgoKAD)

pJC278 (lacZ, lacY)

pJC277 (lacZ, lacY, galD, dgoKAD)

KT2440 (WT)

KT2440 (pJC277)

PpUW42
KT2440 (phaZ-,Lac+)

PpUW43
KT2440 (phaZ-,Lac+,araB$_{Ysn}$)

ENGINEERED MICROORGANISMS FOR SYNTHESIS OF POLYHYDROXYALKANOATES

CROSS REFERENCE TO PRIOR APPLICATIONS

Not applicable.

STATEMENT REGARDING SEQUENCE LISTING

A Sequence Listing associated with this application is electronically submitted herewith in ASCII text file format. The text file containing the Sequence listing is entitled "Sequence_Listing_53813-00103.xml", was created on May 23, 2023, and is 15 kilobytes in size. The Sequence Listing is incorporated herein by reference in its entirety and forms a part of the present specification.

FIELD OF THE DESCRIPTION

The present description relates to microorganisms that are engineered to synthesize polyhydroxyalkanoates, in particular medium chain length polyhydroxyalkanoates. More particularly, the microorganisms described herein are engineered to primarily use simple carbohydrates, in particular lactose, as a carbon source.

BACKGROUND

Plastics are ubiquitous across the world and have a vast number of uses. However, as most plastics are derived from petroleum precursors, the production and disposal of such materials present a host of environmental challenges. Various materials, categorized as biopolymers or bioplastics, have shown promise as eco-friendly, biodegradable, alternatives to synthetic, petroleum-derived plastics. One group of bioplastics that have been investigated are polyhydroxyalkanoates (PHAs).

Polyhydroxyalkanoates (PHAs) are produced naturally as intracellular carbon stores by many bacteria. These biopolymers have garnered attention primarily owing to their wide range of physical properties and potential as a substitute for traditional petrochemical-derived plastics. The inherent biodegradability of PHAs, coupled with the use of biomass as a feedstock for production, makes them a key platform within a Circular Bioeconomy framework. However, compared to fossil-based plastics, PHAs are more expensive to produce.

PHAs are generally categorized according to the monomers that constitute their carbon backbones. Specifically, PHAs formed with C3-C5 monomers are referred to as short chain length (SCL) PHAs, whereas PHAs formed with monomers of C6 or greater are referred to as medium chain length (MCL) PHAs. PHAs may also comprise copolymers of both SCL and MCL monomers. It is known that the physical properties of PHAs are influenced by their monomer composition, which allows for a wide variety of thermal and mechanical properties exhibited by the potential polymers. It is also known that SCL-PHAs are generally brittle and hard, whereas MCL-PHAs are soft and ductile. Therefore, PHAs formed as copolymers of SCL and MCL monomers, with suitable tailoring of the monomers, may serve as replacements for traditional plastics such as polyethylene or polypropylene.

PHAs are synthesized by PHA synthases, which polymerize monomeric hydroxyalkanoate substrates. Substrate specificity varies among PHA producing organisms and the structure of the resulting PHA is influenced by the PHA synthase that is used. PHA synthases have been categorized into four main classes, I to IV. Synthases of Classes I, Ill, and IV generally utilize short chain length monomers, whereas synthases of Class II generally utilize medium chain length monomers. It is known in the art that PHAs comprising different monomeric units, such as mixtures of SCL and MCL hydroxyalkanoates, possess better thermal and physical properties compared with homopolymers.

Although many bacteria are able to produce short chain length (SCL) PHAs, the production of medium chain length PHAs (MCL-PHA) from simple sugar carbon sources, such as those with monomers of C6 and greater, is limited to the microorganisms of the genus *Pseudomonas*. This is correlated with the presence of Class II PHA synthase enzymes and the support pathways that provide the necessary hydroxyalkanoate substrate. For example, *Pseudomonas alloputida* is known to produce medium chain length (MCL) PHA and short chain length (SCL) PHA using simple carbon sources such as glucose.

Various methods have been proposed for improving the efficiency of PHA production in microorganisms and some of these methods comprise genetically engineering certain microbial strains. Examples of known bacterial methods of PHA synthesis are provided, for example, in Kageyama, Y. et al. [13] and Li, Z. et al. [14].

As noted above, one challenge faced in the commercialization of the microbial production of PHAs is the cost of production, which is largely dependent on the feedstock used for the microorganisms. Thus, microorganisms that are capable of utilizing inexpensive or waste carbon products from other processes as a feedstock for PHA synthesis would be desirable. In addition, the choice of feedstock serves another important role in PHA fermentation in that it influences the type of PHA produced.

Thus, microorganisms capable of metabolizing waste carbon products and producing PHAs with MCL monomers (C6 or greater) would be desirable. As discussed further below, it would be particularly desirable if such microorganism were able to use simple carbohydrate feedstock (i.e., mono-, di-, or oligosaccharides) for PHA synthesis.

Lactose is an inexpensive carbon source produced as a plentiful by-product during the production of lactose-free milk and as such would be an ideal candidate feedstock for PHA production. As discussed above, *Pseudomonas alloputida* is able to synthesize MCL PHAs, but this species is unable to utilize lactose or its breakdown product galactose as carbon sources.

Examples of prior efforts to improve the production of PHAs are taught, for example, in EP 0920517, US 2018/0057848, and EP 2886643. These references teach methods of genetically engineering microorganisms for the production of PHAs. However, these known methods fail to teach microorganisms specifically engineered to utilize, for example, lactose as a carbon source.

There is a need for an improved method of microbially producing PHA, in particular MCL PHAs, using a simple carbohydrate feedstock, preferably a waste carbohydrate product such as lactose.

SUMMARY OF THE DESCRIPTION

In one aspect, there is provided a genetically engineered microbial cell that is capable of utilizing a simple carbohydrate feedstock for synthesizing PHAs. In one aspect, the simple carbohydrate is lactose. In another aspect, the genetically engineered cell is a *P. alloputida* cell.

In another aspect, there is provided a unique *P. alloputida* strain comprising cells that are genetically engineered to synthesize PHAs using a simple carbohydrate feedstock, in particular lactose.

In another aspect, there is provided a method of synthesizing PHAs from a simple carbohydrate feedstock, such as lactose, using a genetically engineered microbial cell adapted to metabolize such feedstock.

In another aspect, there is provided a gene construct for use in genetically modifying a microbial host cell to render such cell capable of synthesizing PHAs using a simple carbohydrate feedstock, such as lactose. In one aspect, there are provided DNA sequences coding for a set of proteins that allow lactose utilization in *Pseudomonas alloputida* KT2440.

BRIEF DESCRIPTION OF THE FIGURES

The features of certain embodiments will become more apparent in the following detailed description in which reference is made to the appended figures wherein:

FIG. 5). The strains were grown using (a) 15 mM glucose, (b) 15 mM galactose, and (c) 10 mM lactose as the sole carbon sources.

DETAILED DESCRIPTION

As used herein, the term "simple carbohydrate" will be understood to mean mono-, di-, or oligosaccharides. In one example, a simple carbohydrate would be a disaccharide, such as lactose.

Figures 1, 2:
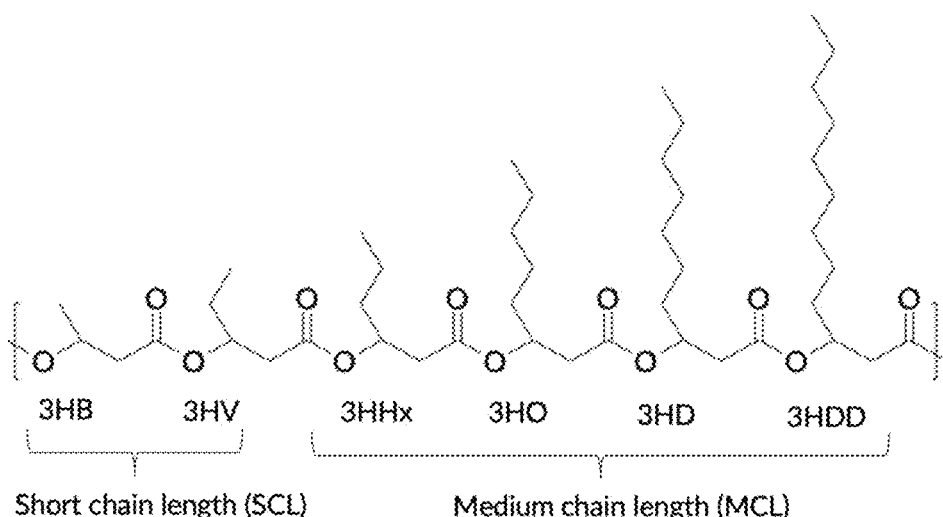
FIG. 1 illustrates examples of different PHA monomer chain lengths.
FIG. 2 illustrates the structure of polyhydroxybutyrate (PHB).

The term polyhydroxyalkanoates, or PHAs, will be understood to mean intracellularly produced polyesters of 3-hydroxyalkanoic acids that are synthesized by microorganisms grown on a feedstock. As discussed above, PHAs can comprise small chain length (SCL) monomers (having a length of C3-C5), medium chain length (MCL) monomers (having a length of C6 or greater, such as, but not limited to, C6-C12 or C6-C14), or long chain length (LCL) monomers (having a chain length greater than C14). PHAs may also comprise copolymers of both forms of monomers. FIG. 1 illustrates examples of different monomer chain lengths. In FIG. 1, the monomers are also identified by conventional nomenclature, where 3HB represents 3-hydroxybutyrate, 3HV represents 3-hydroxyvalerate (or "PHV"), 3HHX represents 3-hydroxyhexanoate (or "PHHx"), 3HO represents 3-hydroxyoctanoate (or "PHO"), 3HD represents 3-hydroxydecanoate (or "PHD"), and 3HDD represents 3-hydroxydodecanoate. Another known MCL monomer is 3-hydroxynonanoate (or "PHN"). By way of example, FIG. 2 illustrates the structure of polyhydroxybutyrate, or PHB, which is a homopolymer of 3HB (a C4 monomer).

The terms "comprise", "comprises", "comprised" or "comprising" may be used in the present description. As used herein (including the specification and/or the claims), and unless stated otherwise, these terms are to be interpreted as open-ended terms and as specifying the presence of the stated features, integers, steps or components, but not as precluding the presence of one or more other feature, integer, step, component or a group thereof as would be apparent to persons having ordinary skill in the relevant art. Thus, the term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

The phrase "consisting essentially of" or "consists essentially of" will be understood as generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open-ended term, such as "comprising" or "including", it will be understood that direct support should be afforded also to "consisting essentially of" language as well as "consisting of" language as if stated explicitly and vice versa. In essence, use of one of these terms in the specification provides support for all of the others.

For the purposes of the present specification and/or claims, and unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth herein are approximations that may vary depending upon the desired properties sought to be obtained by the present invention, inclusive of the stated value and has the meaning including the degree of error associated with measurement of the particular quantity. The term "about" generally refers to a range of numbers that one of ordinary skill in the art would consider as a reasonable amount of deviation to the recited numeric values (i.e., having the equivalent function or result). For example, this term "about" can be construed as including a deviation of ±10 percent of the given numeric value provided such a deviation does not alter the end function or result of the value. Therefore, a value of about 1% can be construed to be a range from 0.9% to 1.1%.

The term "and/or" can mean "and" or "or".

Unless stated otherwise herein, the articles "a" and "the", when used to identify an element, are not intended to constitute a limitation of just one and will, instead, be understood to mean "at least one" or "one or more".

As described herein, the inventors sought to provide a genetically engineered strain of *Pseudomonas* with capability of metabolizing a specific simple carbohydrate feedstock. For this, the inventors thus sought to provide a method of PHA synthesis by utilizing genome engineering to increase the diversity of synthesized PHAs by investigating three areas that influence monomer composition: the carbon source provided, the metabolic profile of the organisms, and the encoded PHA synthase. Functional metagenomics was utilized to isolate enzymes that were found to allow the organism of interest to grow on the desired carbon source and to isolate PHA synthases that achieve varying monomer compositions. Lactose was chosen as an ideal candidate for a feedstock since it is commonly produced as a waste product that it accompanied by waste management issues. It was therefore postulated that taking this negative cost waste product and using it for the production of various PHA copolymers would be a strategy that could potentially make PHAs more cost competitive.

*Pseudomonas alloputida* is a bacterium that has garnered attention as a suitable cellular host for heterologous synthetic reactions [1]. This species remains very versatile in its ability to withstand various environmental conditions and physicochemical stress [2,3]. Common *P. alloputida* isolates such as mt-2 have also been shown to have a role in bioremediation due to their ability to grow on aromatic compounds such as xylene and toluene [1,3]. *P. alloputida* has been used as a chassis for various heterologous pathways because of the range of genetic engineering tools that have been developed for this strain. A noteworthy characteristic of *P. alloputida* is its ability to produce polyhydroxyalkanaotes (PHAs), including native MCL-PHA polymers, and through the introduction of heterologous pathways, SCL-PHA and MCL-SCL copolymers [4].

However, despite its many attributes, *P. alloputida* is limited in its carbon metabolism pathways. Specifically, it lacks the hydrolysis and transport genes for sugars such as galactose, arabinose, xylose, mannose, and lactose [2,5]. These carbohydrate materials may be derived from food waste sources and, therefore, serve as a low cost feedstock [6]. The conversion of food waste sources for the production of added value products has emerged as a way to take many synthetic pathways and embed them into a circular bioeconomy framework. More generally, the ability to upcycle waste material by using it as a feedstock for producing added value materials aids in decreasing the cost of fermentation by providing a low to zero cost feedstock.

Efforts have been made to engineer *P. alloputida* KT2440 to expand its native carbon metabolism, including engineering the strain for galactose, xylose, and arabinose utilization [2,5]. Galactose utilization has been previously accomplished in *P. alloputida* KT2440 by introducing the DeLey Doudoroff (DLD) catabolic pathway for galactose metabolism [2].

For the present study, *Pseudomonas alloputida* was chosen as a suitable candidate because of its ability to host complex heterologous pathways with its versatile metabolism, while also being able to natively produce valuable secondary metabolites such as medium chain length polyhydroxyalkanoates (PHA). An example of a waste carbon source feedstock is the disaccharide lactose, which is a common constituent of dairy waste and was chosen for the present investigation for that reason. However, most *Pseudomonas* species are unable to utilize lactose or its breakdown product galactose. In this work, and as discussed further below, the inventors introduced lactose hydrolase and permease genes, along with the DeLey-Doudoroff catabolic pathway for galactose utilization, into *P. alloputida* strain KT2440 to demonstrate the utilization of lactose as a sole carbon source. The genes introduced by the inventors are listed in Table 1.

TABLE 1

| Lactose and Galactose Utilization genes | | |
| --- | --- | --- |
| Gene | Name | Origin |
| lacZ | β-galactosidase (lactose hydrolase) | *E. coli* K12 |
| lacY | Lactose permease | *E. coli* K12 |
| galD | galactose dehydrogenase | *Pseudomonas* sp. YsS1 |
| dgoK | 2-dehydro-3-deoxygalactonokinase | *Pseudomonas* sp. YsS1 |
| dgoA | 2-dehydro-3-deoxy-6-phosphogalactonate aldolase | *Pseudomonas* sp. YsS1 |
| dgoD | d-galactonate dehydratase | *Pseudomonas* sp. YsS |
| araB | l-arabinolactonase/d-galactonolactonase | *Pseudomonas* sp. MBI-7 |

Thus, in one aspect, there is described herein a unique *P. alloputida* strain, identified herein as PpUW44, having a genome that is engineered to synthesize PHAs utilizing lactose as a sole carbon source.

Figure 3:
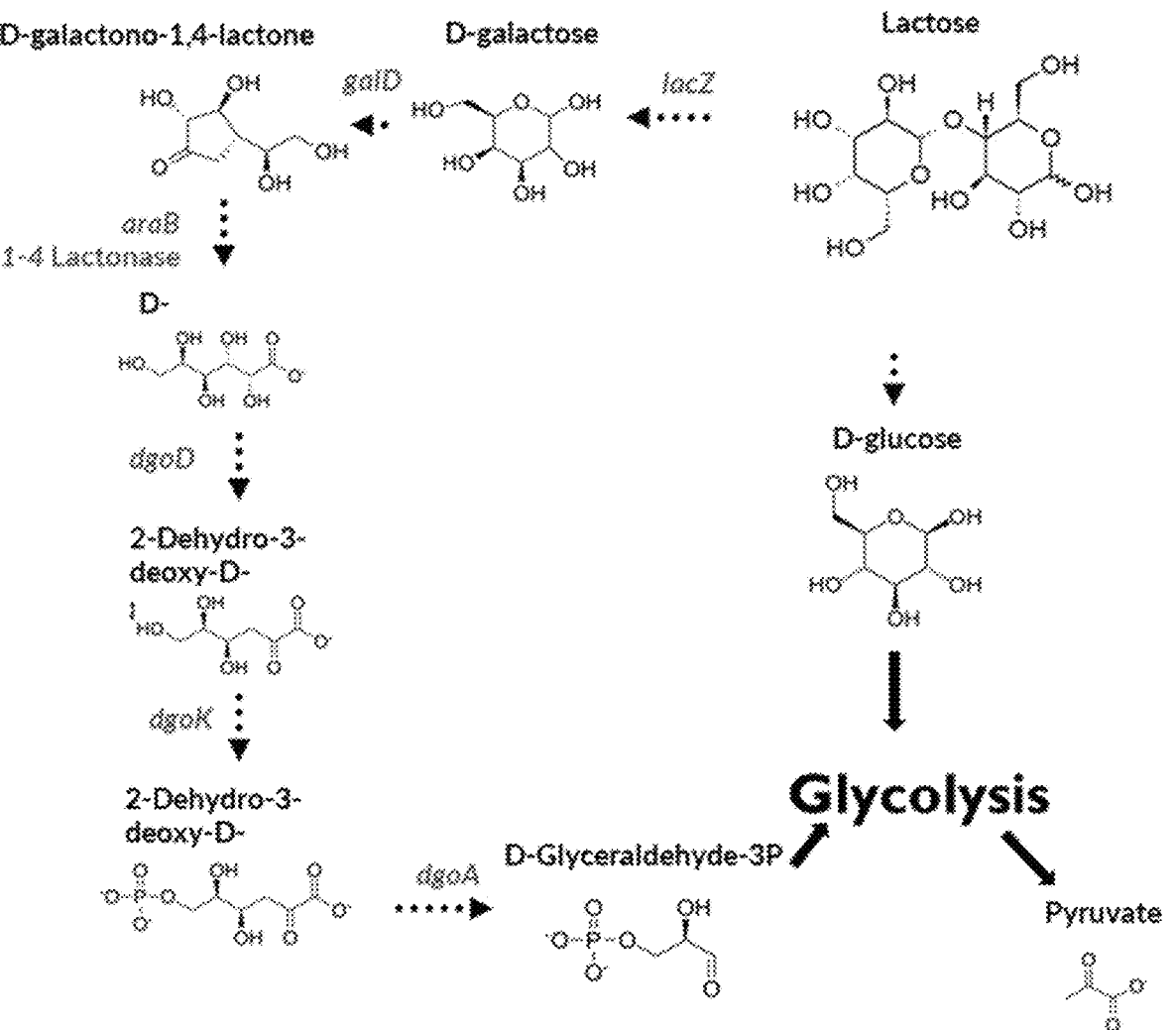
FIG. 3 illustrates the engineered lactose and galactose utilization pathway. lacY, lactose permease, is used to transfer lactose from the media into the cell. lacZ, β-galactosidase (EC 3.1.1.23), galD, galactose dehydrogenase (EC 1.1.1.48), araB, galactonolactonase, dgoK, 2-dehydro-3-deoxygalactonokinase (EC2.7.1.58), dgoA, 2-dehydro-3-deoxy-6-phospho-galactonate aldolase (EC 4.1.2.21), dgoD, and galactonate dehydratase (EC 4.2.1.6), are used for lactose hydrolysis and subsequent galactose hydrolysis. The DeLey-Doudoroff ("DLD") Pathway of galactose metabolism consists of genes galD, araB, dgoKAD.
Figure 4A:
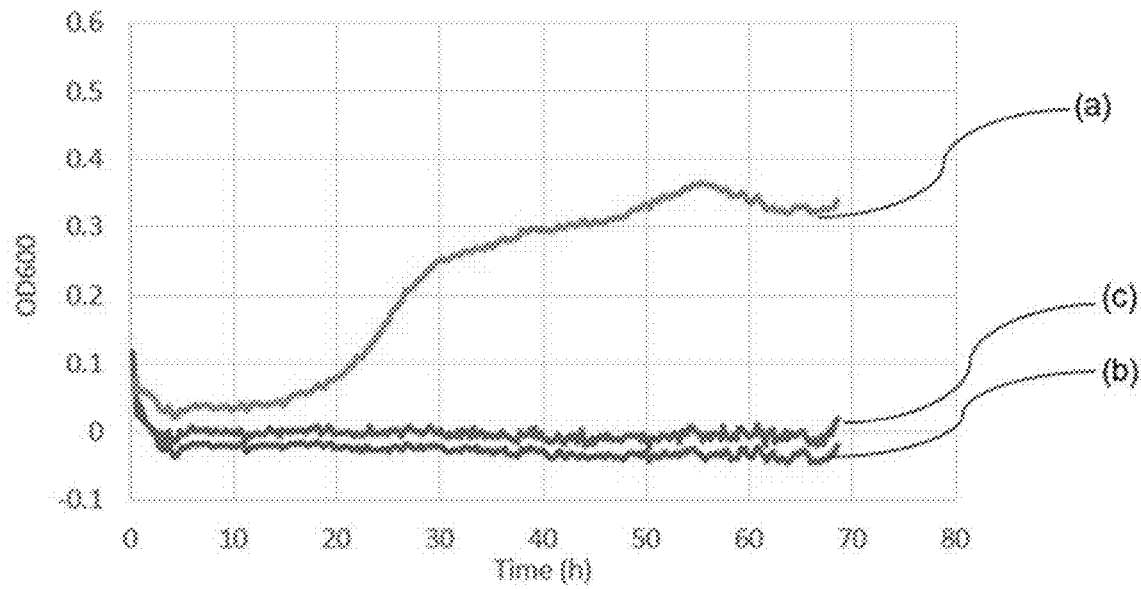
FIGS. 4A to 4D (collectively, FIG. 4) illustrate growth of KT2440 strains containing expression vectors using M63 media supplemented with (a) 15 mM glucose, (b) 15 mM galactose, or (c) 10 mM lactose. 4A: pTH1227 (empty vector); 4B: pJC276 (galD, dgoKAD); 4C: pJC278 (lacZ, lacY); 4D: pJC277 (lacZ, lacY, galD, dgoKAD); 4E: pJC281 (lacZ, lacY, galD, dgoKAD, no laclq).
Figure 4B:
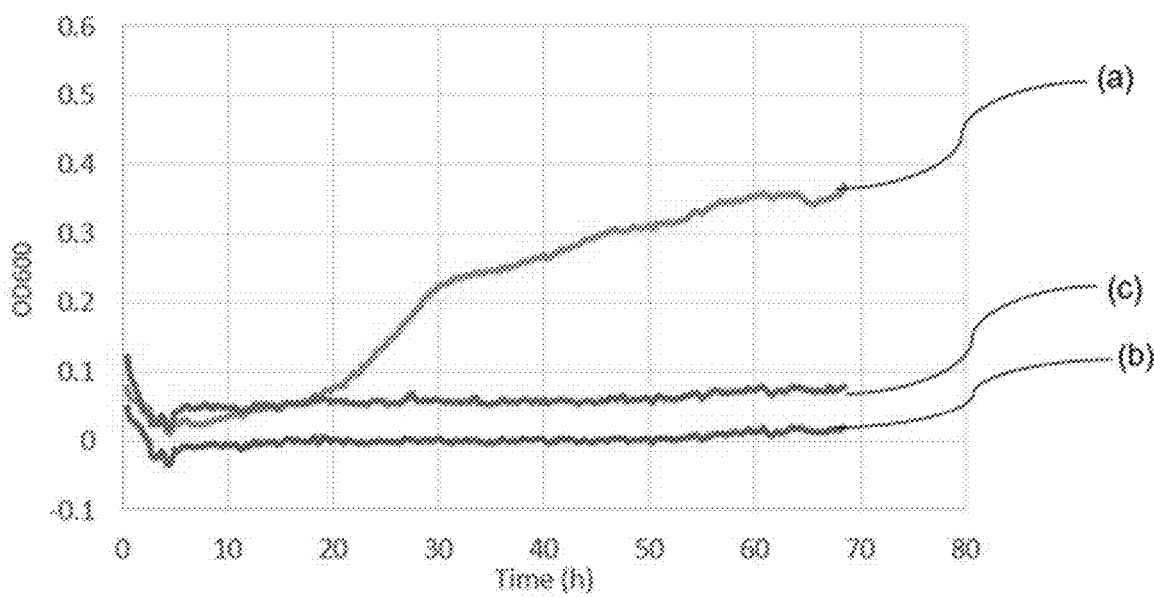
Figure 4C:
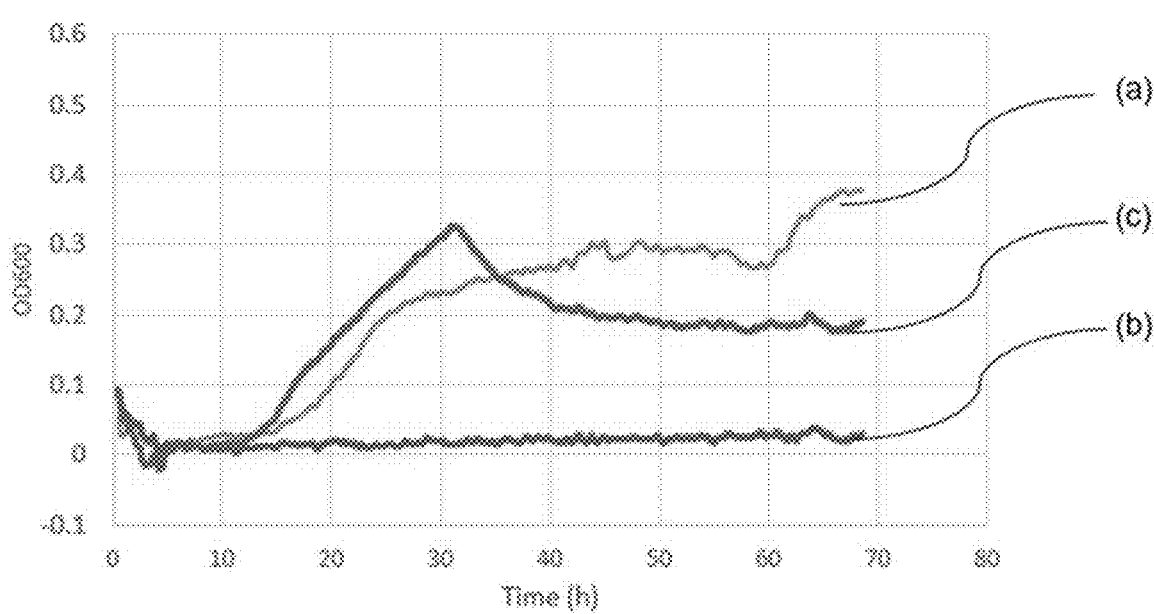
Figure 4D:
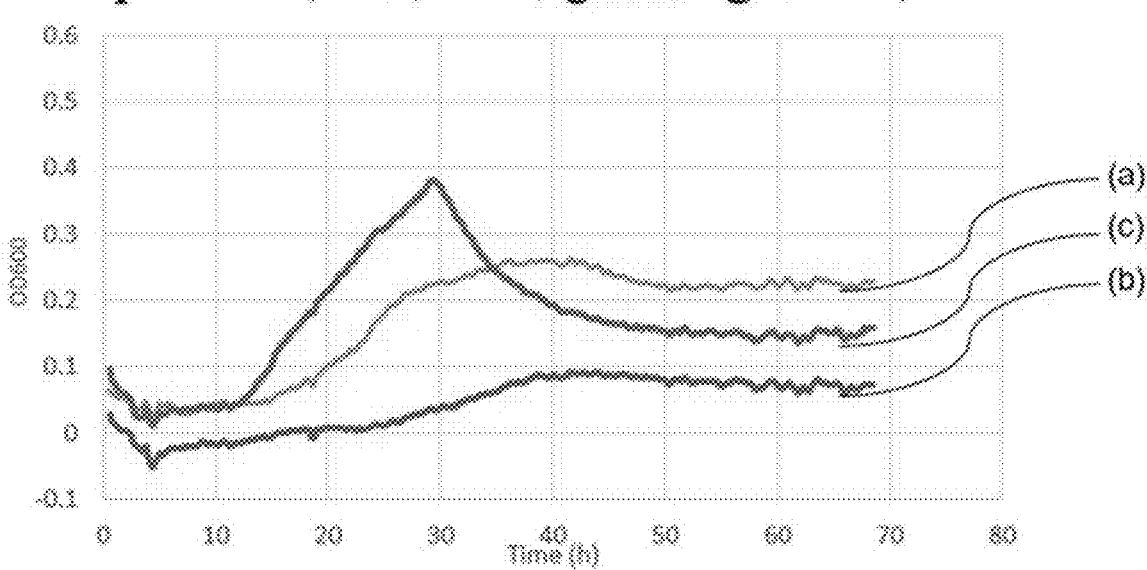
Figure 4E:
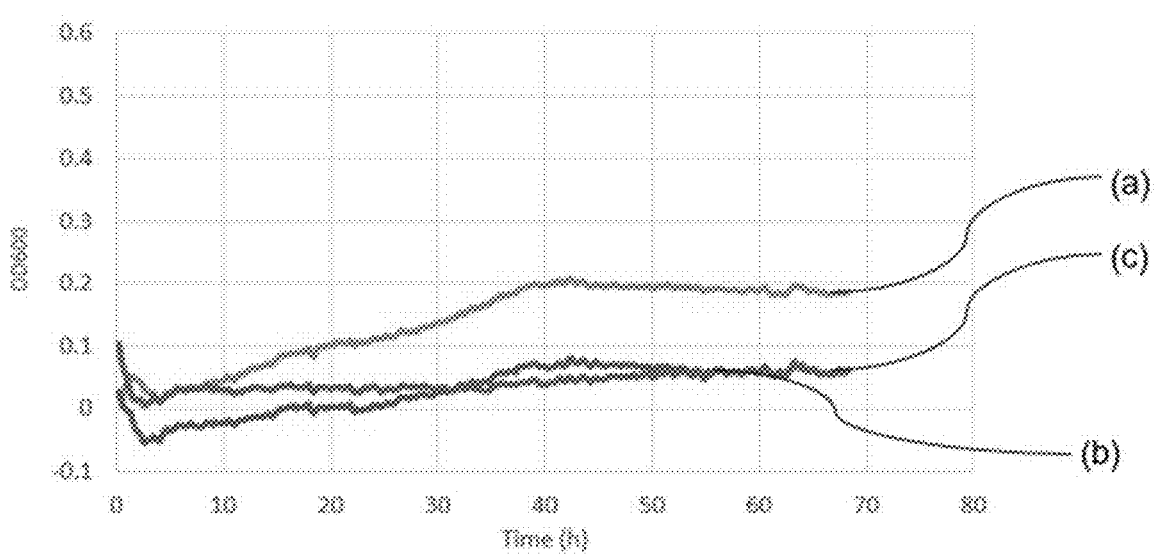

Based on the previous work described above, the present inventors engineered a strain of *P. alloputida* KT2440 (identified herein as PpUW44) that is capable of utilizing lactose as a sole carbon source. The inventors modified the genome of *P. alloputida* KT2440 by integrating predicted lactose and galactose utilization genes therein. To further expand the substrate range of *P. alloputida* KT2440 to include lactose, the inventors constructed a synthetic pathway for the breakdown of galactose and lactose using genes derived from soil isolated microorganisms. The overall lactose and galactose utilization pathway of the presently engineered strain is illustrated in FIG. 3.

The engineering for use of lactose was accomplished by integrating lactose and galactose utilization genes from related organisms into the genome of *Pseudomonas alloputida* KT2440. Functional metagenomic screens were performed to isolate galactose utilization genes in KT2440. Various metagenomically isolated exogenous PHA synthases were introduced into the lactose utilizing strains to demonstrate varying monomer compositions. Thus, the present description provides engineered *P. alloputida* strains that are capable of directly using lactose as feedstock, without pretreatment, for the production of PHAs.

In one aspect, the engineered strains express in a single operon the lactose metabolism pathway and the DeLey-Doudoroff galactose metabolism pathway adapted from *Escherichia coli* and *Pseudomonas* YsS1 and *Pokkaliibacter*

MBI-7 strains to facilitate lactose and galactose metabolism to supplement the native glucose metabolism of strain KT2440. The resulting KT2440 strain was found to be capable of producing both short chain length (SCL) and medium chain length (MCL) PHAs using lactose as a sole carbon source, without requiring pretreatment of such lactose source.

The present description is further illustrated by the following examples.

Results and Discussion

1) Growth on Lactose is Improved by the Introduction of Galactose Utilization Genes galD, dgoKAD Wild type *P. alloputida* KT2440 does not grow on lactose or its breakdown product galactose, so we started by assessing expression of the lacZand lacYgenes from *E. coli* K12 in KT2440. These lactose catabolism and transport genes from *E. coli* have shown to be functional in *Pseudomonas alloputida* KT2440 [7]. The DeLey-Doudoroff, or DLD, pathway for galactose utilization has been previously engineered into KT2440, using genes isolated from *Burkholderia ambifaria* and *Pseudomonas fluorescens* [2].

3) PHA Synthesis from Lactose Using PpUW44

The engineered PpUW44 containing the native phaC (PHA synthase) operon in KT2440 was found to synthesize MCL-PHA. The polymer produced contains 15% poly-3-hydroxyoctanoate (C8) and 86% poly-3-hydroxydeconate (C10). This quantity of PHA is higher than that when grown with gluconic acid. These results demonstrate the first examples of MCL-PHA being synthesized using lactose as a sole carbon source.

Additional experiments were performed to investigate optimal conditions for PHA production and biomass production by varying the carbon to nitrogen ratio. Small fermentations of 100 mL reactions were completed in 1 L flasks. The results of such experiments are summarized in Tables 2 and 3 below. Table 2 summarizes the effect of varying C:N ratios in Ramsay's medium on the biomass yield of PpUW44 using 100 mL shaking flasks cultures. The desired C:N ratio was achieved using varying amounts of ammonium sulfate. Table 3 summarizes the effect of varying C:N ratios in Ramsay's cultures on the conversion rate of lactose to PHA.

TABLE 2

| | | | | | | Total |
|---|---|---|---|---|---|---|
| | Weight of dried | % Biomass | % Biomass | PHO Yield | PHD Yield | PHO/PHD |
| Condition | biomass (g) | PHO | PHD | (mg) | (mg) | (mg) |
| C:N of 4.2 | 0.2449 | 0.840 | 1.496 | 2.057 | 3.665 | 5.722 |
| C:N of 10.5 | 0.2905 | 0.804 | 1.280 | 2.336 | 3.7190 | 6.055 |
| C:N of 21 | 0.2298 | 3.15347 | 12.4676 | 7.2467 | 28.650 | 35.897 |
| C:N of 42 | 0.1778 | 8.609 | 36.155 | 15.306 | 64.284 | 79.591 |

Effect of C:N Ratios on Biomass and PHA Production using PpUW44

Figure 5:
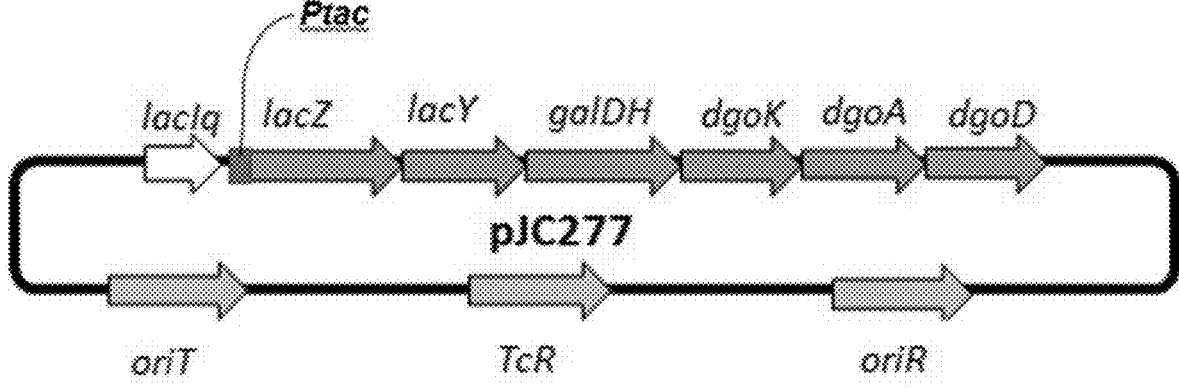
FIG. 5 is a schematic of plasmid pJC277, which contains Lactose cassette v1 (lacZY, galD, dgoK, dgoA, dgoD).
Figure 6A:
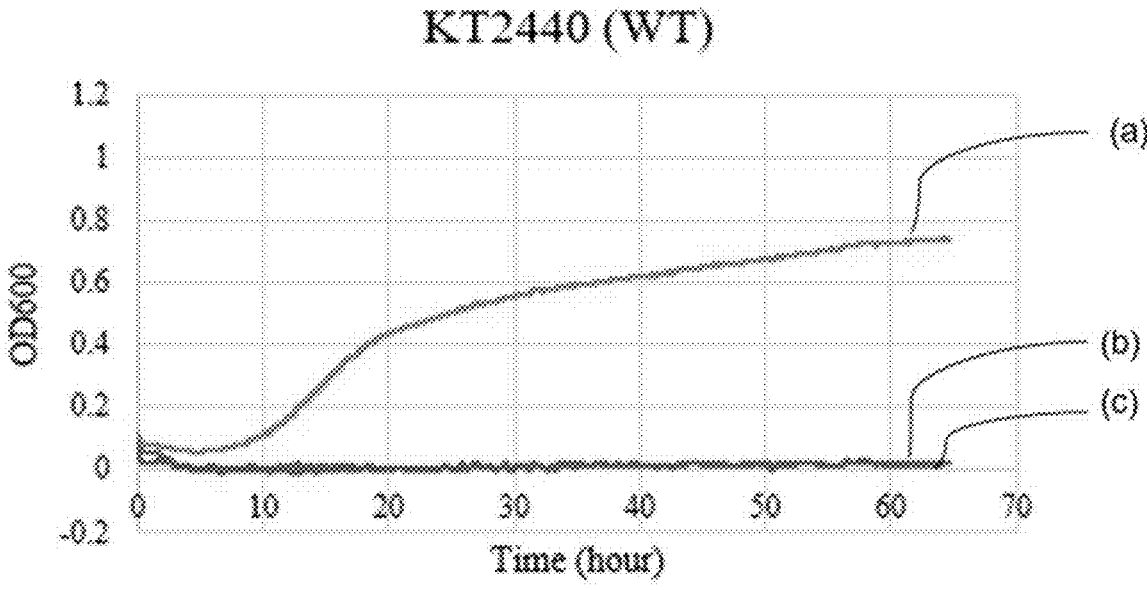
FIGS. 6A to 6E (collectively, FIG. 6) illustrate the growth of genome engineered strains. 6A: KT2440 (wild type); 6B: KT2440 (pJC277); 6C: PpUW42 (KT2440 (phaZ−, Lac+)); 6D: PpUW43 (KT2440 (phaZ−, Lac+, araB$_{YsS1}$)); 6E: PpUW44 (KT2440 (phaZ−, Lac+, araB$_{MBI-7}$)). Lac+ refers to strains with Lactose cassette v1 (from plasmid pJC277.
Figure 6B:
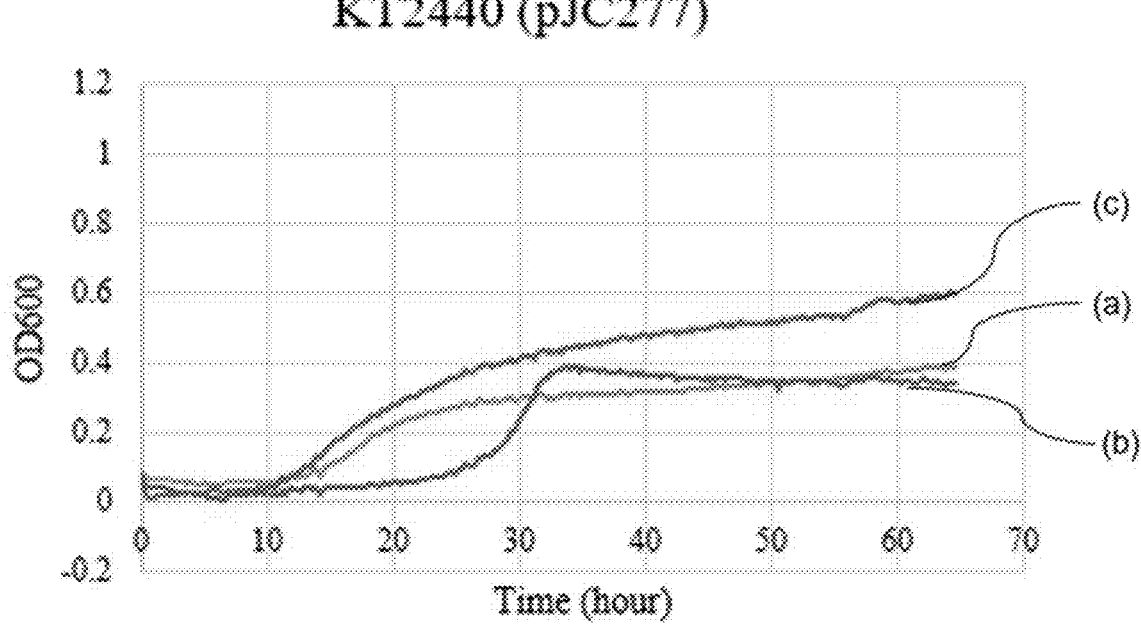
Figure 6C:
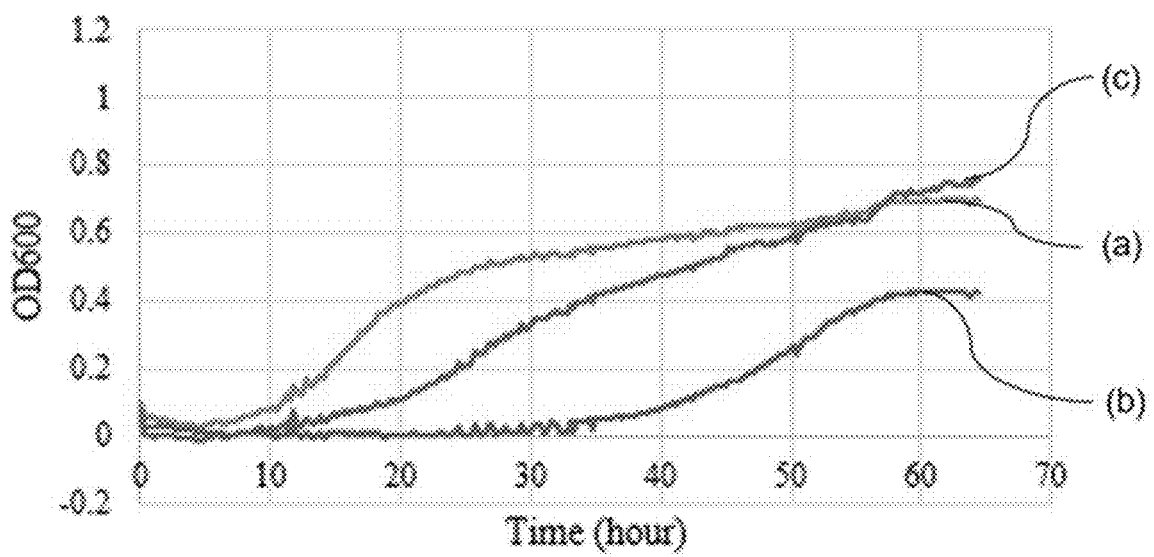
Figure 6D:
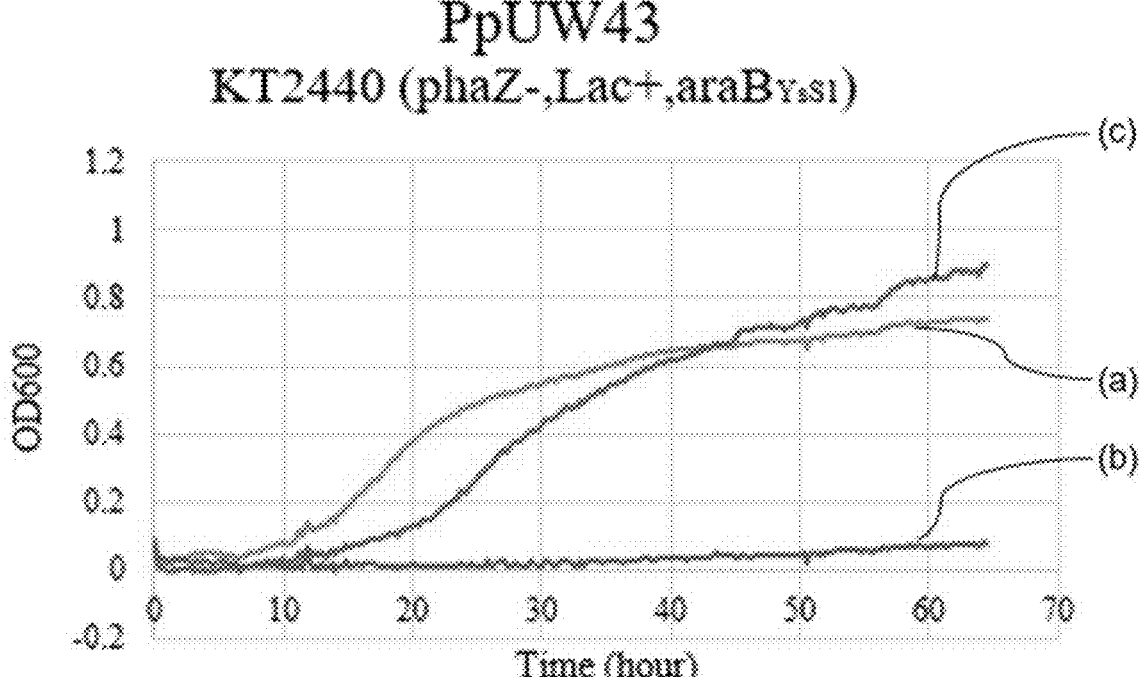
Figure 6E:
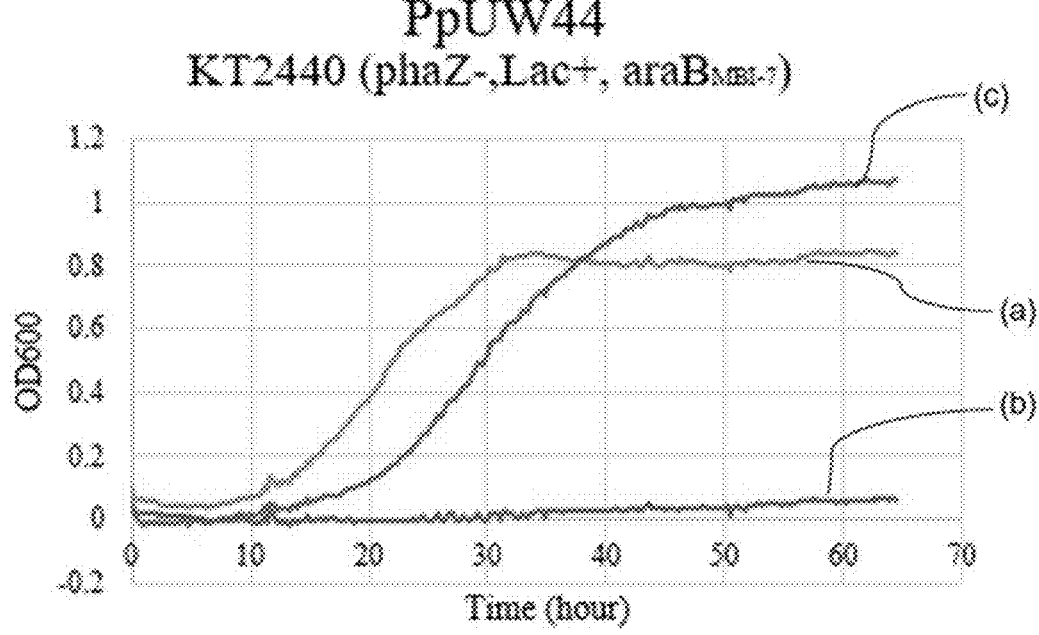

Given the inability of KT2440 to grow on lactose, we hypothesized that the combination of lactose and galactose utilization genes introduced into KT2440 will allow for improved lactose utilization compared to solely introducing in lacZY. We introduced these genes on an expression vector pTH1227, with a strong tac promoter. We inoculated the KT2440 containing plasmid pJC277 (see Table 5 below) into a minimal medium with lactose as a sole carbon and energy source and observed improved growth when the galactose genes are present. These results are presented in FIGS. 4A to 4D (collectively, FIG. 4). A schematic illustrating plasmid pJC277 is shown in FIG. 5.

2) Introduction of araB Further Improves Lactose Utilization

A lactose cassette (Lactose cassette v1, see FIG. 5) including lacZY, galD, and dgoKAD, was integrated into the genome of KT2440. We observed the lack of a 1-4 lactonase in the KT2440 genome. This gene is required in order to have a complete pathway for galactose utilization. Two candidates were chosen for the araB gene, including the 1-4 arabinolactonase from *Pseudomonas* sp. YsS1 (Genbank accession No. CP123771) and the galactonolactonase from *Pokkaliibacter* sp. MBI-7 (Genbank accession No. JARVTG000000000.1). These were integrated downstream of the dgoD gene in Lactose cassette v1 (FIG. 5) to construct PpUW43 (with the YsS1 lactonase) and PpUW44 (with the MBI-7 lactonase). The growth in minimal media was compared between the various strains and it was observed that growth of KT2440 on lactose is improved with the full set of genes present (see FIGS. 6A to 6E). The galactonolactonase from MBI-7 performed better of the two tested lactonases.

TABLE 3

Effect of C:N Ratios on the % Conversion of Lactose to PHA using PpUW44

| Condition | Lactose (g) | PHA (g) | % conversion lactose to PHA |
|---|---|---|---|
| C:N of 4.2 | 0.91 | 0.005723 | 0.628876021 |
| C:N of 10.5 | 0.91 | 0.006056 | 0.665468252 |
| C:N of 21 | 0.91 | 0.035897 | 3.944772509 |
| C:N of 42 | 0.91 | 0.079592 | 8.746347703 |

Overall, it was observed that a higher C:N ratio (e.g., 42) provides for improved PHA production (i.e., a higher conversion of lactose to PHA), while a lower C:N ratio (e.g., 10.5) is better for biomass production.

4) PHA Monomer Composition Synthesized from Lactose Using Heterologously Expressed PHA Synthases on Cosmid Clones A PHA negative strain was constructed by replacing the native PHA operon with an RFP fluorescence cassette. Cosmid clones previously isolated by Cheng and Charles (2016) [4] were conjugated into PpUW49 (a description of which follows below) and the monomer composition of these clones was assessed on lactose as a sole carbon source (Cheng and Charles 2016). The results are shown in Tables 4a and 4b and in FIG. 8.

TABLE 4a

| | PHA and Biomass Yield of strains PpUW53, PpUW54, and PpUW55 when grown on lactose as the sole carbon source | | | | | |
|---|---|---|---|---|---|---|
| Strain | Weight of dried biomass (g) | PHO Yield (g) | PHD Yield (g) | PHB Yield (g) | PHV Yield (g) | Total PHA (g) |
| PpUW53 | 0.3172 | 0.0000 | 0.0000 | 0.0154 | 0.0160 | 0.0314 |
| PpUW54 | 0.2307 | 0.0214 | 0.0045 | 0.0000 | 0.0206 | 0.0464 |
| PpUW55 | 0.2319 | 0.0191 | 0.0334 | 0.0000 | 0.0234 | 0.0760 |

TABLE 4b

| | PHA and Biomass Yield of strains PpUW53, PpUW54, and PpUW55 when grown on lactose as the sole carbon source | | |
|---|---|---|---|
| Strain | PpUW53 | PpUW54 | PpUW55 |
| Weight of dried biomass (g) | 0.3172 | 0.2307 | 0.2319 |
| PHB (%) | 4.83 | — | — |
| PHV (%) | 5.03 | 9.85 | 10.11 |
| PHHx (%) | — | 7.9 | — |
| PHO (%) | — | 9.93 | 8.26 |
| PHD (%) | — | 0.96 | 14.39 |
| Total PHA (%) | 9.9 | 28.005 | 32.75 |

Descriptions of the strains listed in Table 4 are provided later in this description. These strains were engineered with different PHA synthases.

Figure 8:
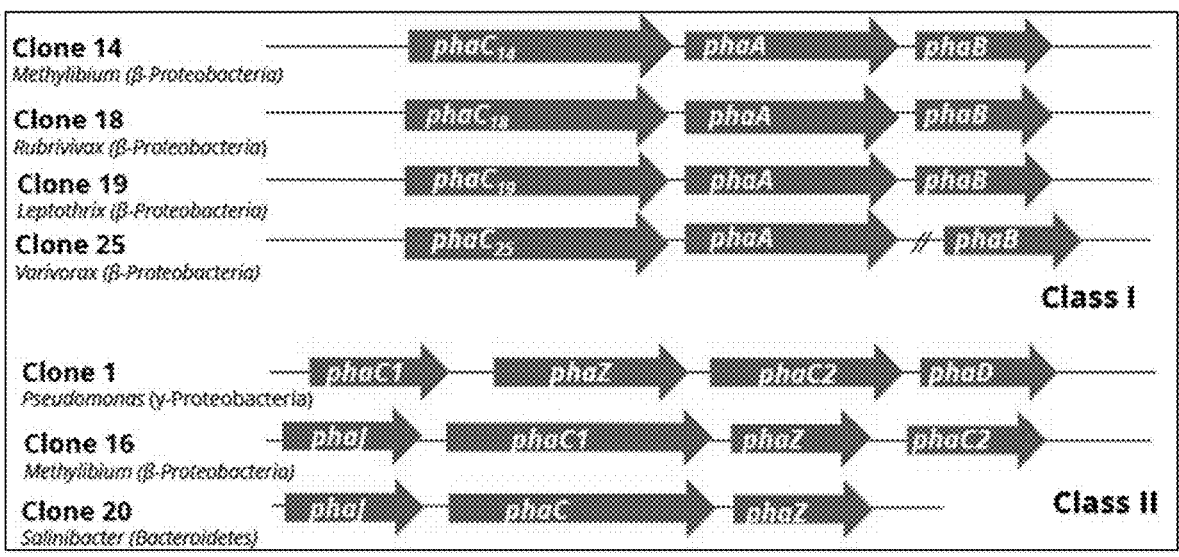
FIG. 8 illustrates PHA synthase containing metagenomic clones that were incorporated into engineered lactose utilizing strains.

Clone 20 (in PpUW55) and Clone 16 (in PpUW54) comprise Class II PHA synthases, which predominantly synthesize MCL-PHA. Clone 14 (in PpUW53) comprises a Class I PHA synthase, which predominantly synthesizes SCL-PHAs. Clones 14, 16, and 20 are schematically illustrated in FIG. 8. As summarized in FIG. 9, it is observed that strains PpUW55 (Clone 20) and PpUW54 (Clone 16) are able to synthesize MCL-SCL copolymers using lactose as a sole carbon source, while strain PpUS53 (Clone 14) is able to synthesize SCL-PHA. As known, the carbon source supplied to the strain has a strong effect on the composition of the final PHA that it produces. It has previously been shown by Cheng and Charles that the monomer composition of the PHA negative strain of KT2440 with these cosmid clones varies depending on the carbon source provided.

Figure 9:
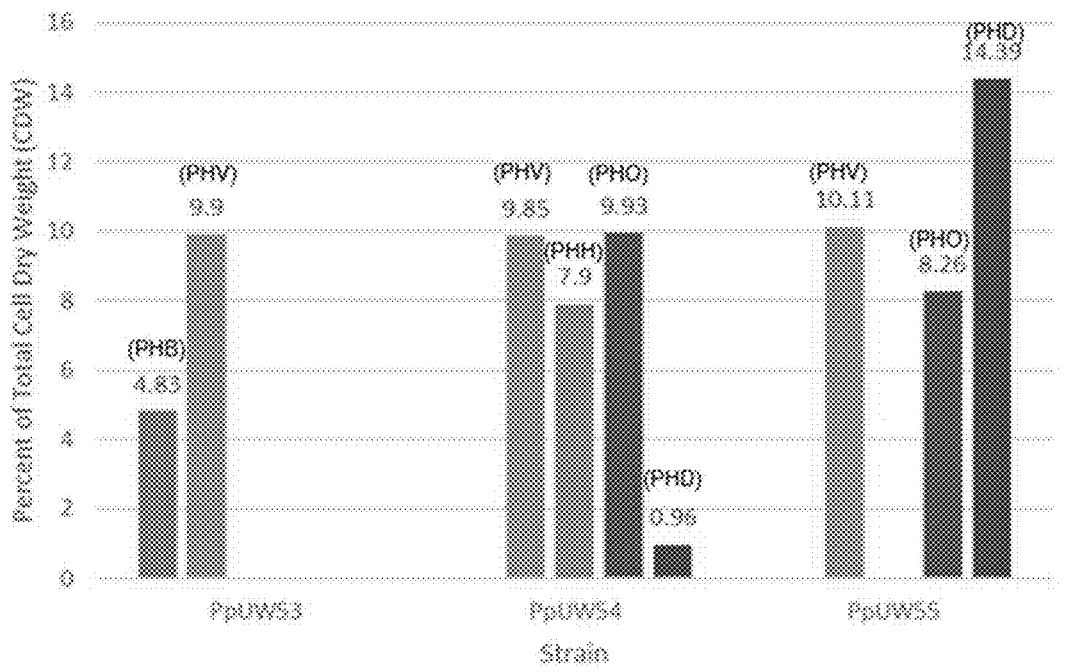
FIG. 9 shows the monomer composition of copolymers produced by genetically engineered *P. alloputida* strains when grown on lactose as the sole carbon source.

As shown in FIG. 9, PpUW53 produces a 3HB:3HV (47:53) SCL-PHA copolymer. This is comparable to the results previously observed for KT2440 (PHA−) with clone 14, where the production is predominantly 3HB, specifically copolymer 3HB (98.9%):3HV(1.1%). Using lactose produces exclusively SCL-PHA copolymer.

PpUW54 produces a 3HV:3HHx:3HO:3HD (34:27:32:7) SCL-MCL PHA copolymer (FIG. 9). This is varied compared to the results previously observed for KT2440 (PHA−) with Clone 16. KT2440 (PHA−) with Clone 16 results in the production of a SCL-MCL copolymer, 3HB:3HHx:3HO (17:39:44). Using lactose as a sole carbon source notably shifts the monomer composition toward MCL-PHA.

PpUW55 produces a 3HV:3HO:3HD (31:25:44) SCL-MCL PHA copolymer (FIG. 9). This is comparable to the results previously observed for KT2440 (PHA−) with Clone 20 which results in the production of predominantly 3HHx: 3HO copolymer. Using lactose shifts this strain to the production of SCL-MCL PHA copolymer.

Conclusion

As described herein, we have demonstrated that it is possible to develop a new engineered strain of *P. alloputida*, KT2440, that is able to use lactose as a sole carbon source for production of PHAs. In this study, we modified the genome of *P. alloputida* to introduce the lacZY genes for lactose hydrolysis and transport, and genes from the DLD pathway, to result in a strain that has improved lactose utilization.

The PHA composition of the native PHA synthase using lactose as a sole carbon source is solely MCL-PHA. The ability to produce MCL-PHA from inexpensive carbon sources, in particular simple sugars such as lactose, is valuable for making the process of PHA synthesis more cost efficient. Substituting raw material used as feedstocks, which are usually purpose-grown, with low-cost waste feedstock can potentially make PHA more cost competitive with synthetic plastics.

We have also demonstrated the production of various PHA copolymers using lactose by introducing different PHA synthases into previously isolated metagenomically isolated cosmid clones. This opens up the potential for creating polymers closer to the characteristics of traditional petroleum based plastics. Availability of a variety of monomer compositions is desirable to pinpoint the blends that will be suited for commercial use. Thus, the present method permits the biosynthesis of various types of PHAs, having physical properties that can be adjusted to suit desired purposes.

The work described herein demonstrates the suitability of *P. alloputida* as a valuable host strain for PHA production by expanding its feedstock substrate range.

Materials and Methods

Bacterial Strains, Plasmids and Growth Conditions

Bacterial strains and plasmids used in the present study are listed in Table 5.

TABLE 5

| Strains and plasmids used | | |
|---|---|---|
| Strains and Plasmids | Relevant Characteristics | Reference |
| pTH1227 | pFUS1 carrying lacIq - Ptac DNA from pMal-c2x (AB32193/AB32194), Tc r | [10] |
| pK19mobsacB | KmR, lacZa, sacB | [11] |
| pJC262_2 | pTH1227 galD | This work |
| pJC276 | pJC262_2 dgoKAD | This work |
| pJC277 | pJC276 lacZY | This work |
| pJC278 | pTH1227 lacZY | This work |
| pJC283 | | This work |
| pJC-MC1 | | This work |
| pAT1 | | This work |
| pAT16 | | This work |
| pRK600 | pRK2013 tra NmR::Tn9, CmR | [12] |
| PpUW1 | RifR mutant | [4] |
| PpUW25 | PpUW1: ΔphaZ | This work |
| PpUW42 | PpUW25: lacZY, dgoKAD, galD | This work |
| PpUW44 | PpUW42: araB | This work |

11

The primer sequences used in this study were synthesized by Integrated DNA Technologies, Inc. and are listed in Table 6.

TABLE 6

Primers used

| Primer Name | Sequence (5' to 3') | SEQ ID NO. |
|---|---|---|
| JC527 | GGACGGTACCAGGAGTCATCGATGCAACCGATTCGTCTC | 1 |
| JC528 | GCGCGAATTCCTAGTCGTAGAACGGTTCAACCGAC | 2 |
| JC525 | AAGAGAATTCAGGAGAAGCGGATGCAGGCGCAATTGATCGCGCTCGA | 3 |
| JC526 | CGCGTCTAGACACTCACCACTCAGCAAACTACCAT | 4 |
| JC523 | TTTCCTCGAGGAGACAGCTATGACCATGATTACGGATTCACTG | 5 |
| JC524 | CACTGGTACCTTAAGCGACTTCATTCACCTGACGACGCAG | 6 |
| JC531 | CGCGGCTTACGCGCTGGCATGAACAATGGACT | 7 |
| JC532 | CGCGTCTAGATTGAAAGCTTCAGATTACTGCGGCGCGTCCGCCGGAAAG | 8 |
| JC533 | CGCGTCTAGAGCGGCTCTGGCTCAGGCCAGGGCCTTGT | 9 |
| JC534 | GCGCGAATTCAGCTTCAAGGCATCGAGCTCGCTGA | 10 |
| JC510 | GCGCAAGCTTATCAACAAGTTCTACGTGTTCGAC | 11 |
| JC511 | ATTTCCCCTGTCAGGCCGCAGCTGTTTCAACGCTCGTGAACGTAGGTGCCTG | 12 |
| JC512 | CAGGCACCTACGTTCACGAGCGTTGAAACAGCTGCGGCCTGACAGGGGAAAT | 13 |
| JC513 | GCGCGGATCCCTTGGCCGCTTCGATGGTCTGCTC | 14 |
| JC514 | GCGCGCGGTGGTTGCACTGGCAGAGTT | 15 |

As discussed further below, the sequences shown in bold and underlining in Table 6 comprise ribosomal binding sites.

*E. coli* strains were grown in Luria Bertani medium (LB) at 37° C. *P. alloputida* was grown in Luria Bertani medium (LB) at 30° C. Utilization of lactose was tested aerobically in Ramsays™ minimal media [8,9]. Antibiotics were used at the following concentrations: tetracycline, 10 µg/ml for *E. coli*; kanamycin, 50 µg/ml for *P. alloputida*; 25 µg/ml for *E. coli*; triclosan, 25 µg/ml for *P. alloputida.*

Strain Construction

1) Construction of pJC277

Cloning Galactose Dehydrogenase

The gene encoding a putative galactose dehydrogenase (EC 1.1.1.48) in *Pseudomonas* sp. YsS1, Genbank accession no. QCD61_16410, was PCR amplified using primers JC527 and JC528. A ribosomal binding side (AGGAG) was incorporated in primer JC527. The DNA fragment of 923 bp was digested with restriction enzymes Kpnl and EcoRI and then inserted into the Kpnl and EcoRI sites in plasmid pTH1227 to obtain pJC264_2.

Cloning Galactonate Degradation Genes

The genes QCD61_19540, QCD61_19535, and QCD61_19530 (Genbank) in *Pseudomonas* sp. YsS1, encoding putative 2-dehydro-3-deoxy-galactonokinase (dgoK, EC 2.7.1.58), 2-dehydro-3-deoxy-6-phosphogalactonate aldolase (dgoA, EC 4.1.2.21), and galactonate dehydratase (dgoD, EC 4.2.1.6), were obtained by PCR amplification using primer pair JC525 and JC526. A ribosomal binding site (AGGAG) was added in the forward primer JC525. The 2,854-bp fragment was restricted with EcoRI and Xbal and inserted into the EcoRI and Xbal sites in pJC264_2, yielding plasmid pJC276.

Cloning *E. coli* lacZY Genes

The lacZY genes encoding for β-galactosidase (EC 3.1.1.23) and lactose permease were PCR amplified from *E. coli* W3110 with primers JC523 and JC524. A ribosomal binding site (GAGGAG) was engineered in primer JC523. The 4,409-bp DNA fragment was restricted with Xhol and Kpnl, and then inserted into the Xhol and Kpnl sites in pTH1227 and pJC276 to obtain plasmids pJC277 and pJC278, respectively.

2) Construction of pJC283 and pAT1

The chosen insertion site is between genes PP_5009 and PP_5010 in *P. alloputida* KT2440. Specifically, 5 bp downstream of the open reading frame of PP_5009. pK19mobsacB was digested with HindIII and then treated with the Klenow fragment to blunt the cut HindIII site. The blunted and linearized plasmid was then cut with restriction enzyme Xbal. A DNA fragment in the region upstream of the insertion site (1989 bp) was PCR amplified using *P. alloputida* KT2440 genomic DNA as a template using primers JC531 and JC532. The fragment was then digested with Xbal and then cloned into the prepared pK19mobsacB plasmid to construct pJC279. A DNA fragment in the region downstream of the insertion site (1747 bp) was PCR amplified using *P. alloputida* KT2440 genomic DNA as a template using primer JC533 and JC534, digested with Xbal and EcoRI, and then cloned into the Xbal and EcoRI sites in pJC279 to construct pJC283.

The lactose cassette from pJC277 was digested using HindIII and Xbal and inserted into the same sites in pJC283 to construct plasmid pAT1.

3) Construction of PpUW25 (KT2440 AdphaZ)

A DNA fragment (1,044 bp) upstream of the phaZ(poly (3-hydroxyalkanoate) depolymerase) gene (PP_5004) in *P. alloputida* KT2440 was PCR amplified with primer pair JC510 and JC511. Another region (1,128 bp) downstream of the phaZgene was obtained by PCR amplification with primers JC512 and JC513. The two fragments were gel purified, combined in equal amounts, and amplified with primers JC510 and JC513. The 2,124-bp product was restricted with HindIII and BamHI, and then inserted into the HindIII and BamHI sites in pK19mobsacB to obtain plasmid pJC-MC1 (which may also be referred to herein as "pJCΔphaZ"). The in-frame deletion of phaZgene was verified by Sanger sequencing with primer JC514.

The plasmid pJC-MC1 was conjugated into *P. alloputida* PpUW1 with helper plasmid pRK600. A trans conjugate was streak purified once on a LB plate (Rif Km). A single colony was grown in LB overnight, diluted serially and plated on LB media containing 5% sucrose. Suc$^R$ colonies were patched on both LB and LB (Km) plates. Genomic DNA was isolated from Km$^S$ colonies, and used for PCR amplification with primers JC514 and JC513. The products were resolved on 1% TAE agarose gel. The strain having a 1,234-bp PCR product (phaZ−) was saved as PpUW25.

4) Construction of PpUW42: KT2440 (phaZ−, Lac+)

Plasmid pAT1 was conjugated into PpUW25 in a triparental mating using helper plasmid pRK600. Single crossover recombination of pAT1 was selected with Km and Tri. A double crossover recombination event was achieved by growing a Km$^R$ Tri$^R$ colony on LB Tri X-gal supplemented with 10% sucrose. The strains with successful integration appear blue on X-gal. The resulting strain was also verified using colony PCR and by examining Km sensitivity.

5) Construction of PDUW43: KT2440 (phaZ−, Lac+, araB$_{YsS1}$)

A DNA sequence with the QCD61_19590 gene araB (EC 3.1.1.15) in YsS1 was synthesized (BioBasic™) with 500 bp upstream and downstream regions to insert downstream of the galD gene in PpUW42. The synthesized sequence was cloned into pK19mobsacB to construct plasmid pAT15.

Plasmid pAT15 was conjugated into PpUW42 in a triparental mating using helper plasmid pRK600. Single crossover recombination of pAT15 was selected with Km and Tri. A double crossover recombination event was achieved by growing a Km$^R$ Tri$^R$ colony on LB Tri supplemented with 10% sucrose. The resulting strain was verified using colony PCR and by examining Km sensitivity.

6) Construction of PpUW44: KT2440 (phaZ−, Lac+, araB$_{MBI7}$)

A DNA sequence with the QCD60_17570 gene araB (EC 3.1.1.25) in MBI-7 was synthesized (BioBasic™) with 500 bp upstream and downstream regions to insert downstream of the galD gene in PpUW42. The fragment was cloned into pK19mobsacB to construct plasmid pAT16.

Figure 7:
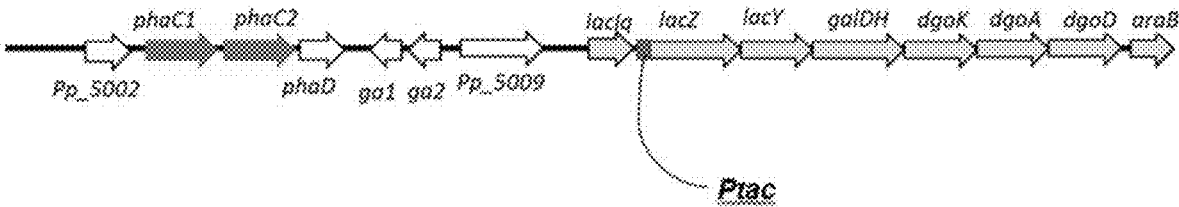
FIG. 7 illustrates the gene construct PpUW44 (KT2440: ΔphaZ, lacZY, galD, dgoKAD, araB$_{MBI-7}$).

Plasmid pAT16 was conjugated into PpUW42 in a triparental mating using helper plasmid pRK600. Single crossover recombination of pAT16 was selected with Km and Tri. A double crossover recombination event was achieved by growing a Km$^R$ Tri$^R$ colony on LB Tri supplemented with 10% sucrose. The resulting strain was verified using colony PCR and by examining Km sensitivity. The gene construct PpUW44 is illustrated in FIG. 7.

7) Construction of PpUW49: KT2440 (ΔphaC1ZC2::Rfp, Lac+, araB$_{mbi7}$)

An rfp cassette sequence from plasmid pJH110 (Addgene: 68376) was synthesized (BioBasic™) and flanked with 500 bp upstream and downstream regions of the native PHA operon (phaC1ZC2). The sequence was cloned into pK19mobsacB to construct plasmid pAT3.

Plasmid pAT3 was conjugated into PpUW44 in a triparental mating using helper plasmid pRK600. Single crossover recombination of pAT3 was selected with Km and Tri. A double crossover recombination event was achieved by growing a Km$^R$ Tri$^R$ colony on LB Tri supplemented with 10% sucrose. The resulting strain was verified using colony PCR and by examining Km sensitivity.

8) Construction of PpUW53: KT2440 (ΔphaC1ZC2::Rfp, Lac+, araB$_{mbi7}$)+11AW Clone 14

Cosmid clone 11 AW Clone 14 (Genbank: KT944262) was conjugated into PpUW49 in a triparental mating using helper plasmid pRK600. Transconjugants were selected on Tri and Tet.

9) Construction of PpUW54: KT2440 (ΔphaC1ZC2::Rfp, Lac+, araBm$_b$i7)+11AW Clone 16

Cosmid clone 11AW Clone 16 (Genbank: K944263) was conjugated into PpUW49 in a triparental mating using helper plasmid pRK600. Transconjugants were selected on Tri and Tet.

10) Construction of PpUW55: KT2440 (ΔphaC1ZC2::rfp, Lac+, araB$_{mbi7}$)+11 AW Clone 20

Cosmid clone 11 AW clone 20 (Genbank: KT944271) was conjugated into PpUW49 in a triparental mating using helper plasmid pRK600. Transconjugants were selected on Tri and Tet.

Plate Reader Growth Assay

Single colonies were inoculated into LB, antibiotic was added if the strain had a plasmid introduced. The culture was incubated overnight at 30° C., spinning at 225 rpm. Cells were washed twice in 0.85% and resuspended in M63 medium supplements with 10 μM lactose. Cells were inoculated in M63 media supplemented with lactose to reach a starting OD of 0.05 and a final volume of 900 μL. Three 300 μL replicates were pipetted into wells in 100-well honeycomb plates (Bioscreen™ C). Data was collected using a Bioscreen™ C (Growth Curves USA, Piscataway, USA).

PHA Production, Extraction and Characterization

PpUW44 was grown in 5 mL of LB overnight. The full culture was pelleted and washed in 0.85% NaCl, and then subcultured (1% v/v) in 100 mL Ramsays™ minimal media supplemented with 320 C-mmol lactose. Nitrogen content was controlled to vary the C:N ratio by supplementing (NH$_4$)$_2$SO$_4$ to specific cultures before growth. The cultures were grown at 30° C. and at 225 rpm for 48 hours. The cultures were then pelleted by centrifugation at room temperature and 7745 g for 3 minutes, washed twice with deionized water. The cells were dried at 95° C. for 48 h and the Cell Dry Weight (CDW) was obtained. 10 mg of dried cell biomass or standard was used for PHA methanolysis. The cell pellet was suspended in 2 mL analytical grade chloroform and 2 mL analytical grade methanol acidified with 15% (v/v sulfuric acid). 2 mg benozic acid was added as an internal standard. The contents were mixed thoroughly and incubated at 100° C. for 5 hours. The mixture was cooled to room temperature and washed twice with water, removing the organic layer formed at the bottom each time. Each wash aimed to remove contaminating methanol, sulfuric acid and cell debris. The chloroform phase (2 mL) was collected and passed through a cotton plugged Pasteur pipette that was packed with anhydrous sodium sulfate to remove residual water. The mixture was also passed through a 0.2 μM PTFE filter and collected in a screw cap 2 mL GC vial. 1 μL of methanolyzed sample was analyzed using gas chromatography-mass spectrometry (GC-MS; an Agilent™ 6890 series GC-MS with 5973 Network™ MS detector with a DB-1 MS capillary column). The column flow was 1.4 d mL/min with a run time of 28.50 minutes. The oven temperature was 45° C. with a 3-minute hold then ramping at 10° C./minute to 250° C. and holding for 5 minutes. The monomer composition of the samples was then determined by weight and by ratio to dry cell weight.

Although the above description includes reference to certain specific embodiments, various modifications thereof will be apparent to those skilled in the art. Any examples provided herein are included solely for the purpose of illustration and are not intended to be limiting in any way. Any drawings provided herein are solely for the purpose of illustrating various aspects of the description and are not intended to be drawn to scale or to be limiting in any way. The scope of the claims appended hereto should not be limited by the preferred embodiments set forth in the above description but should be given the broadest interpretation consistent with the present specification as a whole. The disclosures of all references in the present description herein are incorporated herein by reference in their entirety.

REFERENCES

1. Loeschcke A, Thies S. *Pseudomonas putida*—a versatile host for the production of natural products. Appl Microbiol Biotechnol. 2015; 99: 6197-6214.
2. Peabody G L, Elmore J R, Martinez-Baird J, Guss A M. Engineered KT2440 co-utilizes galactose and glucose. Biotechnol Biofuels. 2019; 12: 295.
3. Volke D C, Calero P, Nikel P I. *Pseudomonas putida*. Trends Microbiol. 2020; 28: 512-513.
4. Cheng J, Charles T C. Novel polyhydroxyalkanoate copolymers produced in *Pseudomonas putida* by metagenomic polyhydroxyalkanoate synthases. Appl Microbiol Biotechnol. 2016; 100: 7611-7627.
5. Elmore J R, Dexter G N, Salvachúa D, O'Brien M, Klingeman D M, Gorday K, et al. Engineered *Pseudomonas putida* simultaneously catabolizes five major components of corn stover lignocellulose: Glucose, xylose, arabinose, p-coumaric acid, and acetic acid. Metab Eng. 2020; 62:62-71.

6. Tsang Y F, Kumar V, Samadar P, Yang Y, Lee J, Ok Y S, et al. Production of bioplastic through food waste valorization. Environ Int. 2019; 127: 625-644.
7. Hansen L H, Sorensen S J, Jensen L B. Chromosomal insertion of the entire 4 *Escherichia coli* lactose operon, into two strains of *Pseudomonas*, using a modified mini-Tn5 delivery system. Gene. 1997; 186: 167-173.
8. Sharma P K, Fu J, Cicek N, Sparling R, Levin D B. Kinetics of medium-chain-length polyhydroxyalkanoate production by a novel isolate of *Pseudomonas putida* LS46. Can J Microbiol. 2012; 58: 982-989.
9. Deininger P. Molecular cloning: A laboratory manual. Analytical Biochemistry. 1990. pp. 182-183. doi:10.1016/0003-2697(90)90595-z
10. Cheng J, Sibley C D, Zaheer R, Finan T M. A *Sinorhizobium meliloti* minE mutant has an altered morphology and exhibits defects in legume symbiosis. Microbiology. 2007; 153: 375-387.
11. Schäfer A, Tauch A, Jäger W, Kalinowski J, Thierbach G, Puhler A. Small mobilizable multi-purpose cloning vectors derived from the *Escherichia coli* plasmids pK18 and pK19: selection of defined deletions in the chromosome of *Corynebacterium glutamicum*. Gene. 1994; 145: 69-73.
12. Finan T M, Kunkel B, De Vos G F, Signer E R. Second symbiotic megaplasmid in *Rhizobium meliloti* carrying exopolysaccharide and thiamine synthesis genes. J Bacteriol. 1986; 167: 66-72.
13. Kageyama, Y., Tomita, H., Isono, T., Satoh, T., Matsumoto, K. Artificial polyhydroxyalkanoate poly [2-hydroxybutyrate-block-3-hydroxybutyrate] elastomer-like material. Sci. Reports. 2021; 11:22446.
14. Li, Z., Yang, J., Jun Loh, X. Polyhydroxyalkanoates: opening doors for a sustainable future. NPG Asia Materials. 2016; 8.

We claim:

1. A cell of a microorganism, wherein the cell is genetically modified to synthesize polyhydroxyalkanoates, PHAs, using lactose as the sole carbon source, wherein:

the microorganism is *Pseudomonas alloputida* KT2440; and the microorganism is genetically modified to incorporate in its genome non-native genes for lactose and galactose metabolization, wherein:

the non-native genes are expressed in a single operon;

the non-native genes for lactose metabolization are lacY and lacz obtained from *Escherichia coli*; and the non-native genes for galactose metabolization are galactose dehydrogenase (galD), 2-dehydro-3-deoxy-galactonokinase (dgok), 2-dehydro-3-deoxy-6-phos-pho-galactonate aldolase (dgoA), and galactonate dehydratase (dgoD) obtained from *Pseudomonas* YsS1.

2. The cell of claim 1, wherein the genome of the cell further comprises a non-native gene encoding a lactonase.

3. The cell of claim 2, wherein the lactonase is arabinolactonase or galactonolactonase.

4. The cell of claim 2, wherein the lactonase is galactonolactonase (araB).

5. The cell of claim 2, wherein the gene encoding a lactonase is obtained from *Pseudomonas* sp. YsS1 or *Pokkaliibacter* sp. MBI-7.

6. The cell of claim 1, wherein the cell is further modified to incorporate in its genome one or more non-native genes encoding one or more PHA synthases.

7. The cell of claim 6, wherein the one or more PHA synthases catalyze the synthesis of small chain length PHAs, medium chain length PHAs, or a combination thereof.

8. The cell of claim 2, wherein the cell is further modified to incorporate in its genome one or more non-native genes encoding one or more PHA synthases.

9. The cell of claim 8, wherein the one or more PHA synthases catalyze the synthesis of small chain length PHAs, medium chain length PHAs, or a combination thereof.

10. The cell of claim 1, wherein the cell is genetically modified by a plasmid comprising the non-native genes.

11. The cell of claim 10, wherein the plasmid incorporates at least one promoter.

12. The cell of claim 11, wherein the at least one promoter comprises laclq and/or Ptac.

13. The cell of claim 1, wherein the PHAs comprise short chain length (SCL) and medium chain length (MCL) PHAs.

14. A method of producing a cell according to claim 1, wherein the cell is genetically modified with a vector that directs the expression of a nucleic acid sequence encoding the non-native genes.

15. A method for producing polyhydroxyalkanoates, PHAs, comprising:

culturing the cell of claim 1 in a medium comprising lactose as the only carbon source; and, isolating PHAs synthesized by the cell from the medium.

16. The method of claim 15, wherein the PHAs comprise short chain length (SCL) and medium chain length (MCL) PHAs.

* * * * *

SEQUENCE LISTING

```
Sequence total quantity: 15
SEQ ID NO: 1            moltype = DNA  length = 39
FEATURE                 Location/Qualifiers
source                  1..39
                        mol_type = other DNA
                        organism = synthetic construct
SEQUENCE: 1
ggacggtacc aggagtcatc gatgcaaccg attcgtctc                       39

SEQ ID NO: 2            moltype = DNA  length = 35
FEATURE                 Location/Qualifiers
source                  1..35
                        mol_type = other DNA
                        organism = synthetic construct
SEQUENCE: 2
gcgcgaattc ctagtcgtag aacggttcaa ccgac                           35

SEQ ID NO: 3            moltype = DNA  length = 47
FEATURE                 Location/Qualifiers
source                  1..47
                        mol_type = other DNA
                        organism = synthetic construct
SEQUENCE: 3
aagagaattc aggagaagcg gatgcaggcg caattgatcg cgctcga               47

SEQ ID NO: 4            moltype = DNA  length = 36
FEATURE                 Location/Qualifiers
source                  1..36
                        mol_type = other DNA
                        organism = synthetic construct
SEQUENCE: 4
cgcgtctaga cactcaccac tcagcaaaac taccat                          36

SEQ ID NO: 5            moltype = DNA  length = 43
FEATURE                 Location/Qualifiers
source                  1..43
```

-continued

```
                            mol_type = other DNA
                            organism = synthetic construct
SEQUENCE: 5
tttcctcgag gagacagcta tgaccatgat tacggattca ctg                        43

SEQ ID NO: 6              moltype = DNA   length = 40
FEATURE                  Location/Qualifiers
source                   1..40
                            mol_type = other DNA
                            organism = synthetic construct
SEQUENCE: 6
cactggtacc ttaagcgact tcattcacct gacgacgcag                            40

SEQ ID NO: 7              moltype = DNA   length = 32
FEATURE                  Location/Qualifiers
source                   1..32
                            mol_type = other DNA
                            organism = synthetic construct
SEQUENCE: 7
cgcggcttac gcgctggcat gaacaatgga ct                                    32

SEQ ID NO: 8              moltype = DNA   length = 49
FEATURE                  Location/Qualifiers
source                   1..49
                            mol_type = other DNA
                            organism = synthetic construct
SEQUENCE: 8
cgcgtctaga ttgaaagctt cagattactg cggcgcgtcc gccggaaag                  49

SEQ ID NO: 9              moltype = DNA   length = 38
FEATURE                  Location/Qualifiers
source                   1..38
                            mol_type = other DNA
                            organism = synthetic construct
SEQUENCE: 9
cgcgtctaga gcggctctgg ctcaggccag ggccttgt                              38

SEQ ID NO: 10            moltype = DNA   length = 35
FEATURE                  Location/Qualifiers
source                   1..35
                            mol_type = other DNA
                            organism = synthetic construct
SEQUENCE: 10
gcgcgaattc agcttcaagg catcgagctc gctga                                 35

SEQ ID NO: 11            moltype = DNA   length = 34
FEATURE                  Location/Qualifiers
source                   1..34
                            mol_type = other DNA
                            organism = synthetic construct
SEQUENCE: 11
gcgcaagctt atcaacaagt tctacgtgtt cgac                                  34

SEQ ID NO: 12            moltype = DNA   length = 52
FEATURE                  Location/Qualifiers
source                   1..52
                            mol_type = other DNA
                            organism = synthetic construct
SEQUENCE: 12
atttcccctg tcaggccgca gctgtttcaa cgctcgtgaa cgtaggtgcc tg              52

SEQ ID NO: 13            moltype = DNA   length = 52
FEATURE                  Location/Qualifiers
source                   1..52
                            mol_type = other DNA
                            organism = synthetic construct
SEQUENCE: 13
caggcaccta cgttcacgag cgttgaaaca gctgcggcct gacaggggaa at              52

SEQ ID NO: 14            moltype = DNA   length = 34
FEATURE                  Location/Qualifiers
source                   1..34
                            mol_type = other DNA
                            organism = synthetic construct
SEQUENCE: 14
gcgcggatcc cttggccgct tcgatggtct gctc                                  34

SEQ ID NO: 15            moltype = DNA   length = 27
FEATURE                  Location/Qualifiers
```

-continued

```
source              1..27
                    mol_type = other DNA
                    organism = synthetic construct
SEQUENCE: 15
gcgcgcggtg gttgcactgg cagagtt                                        27
```